(12) United States Patent
Roach et al.

(10) Patent No.: US 11,344,723 B1
(45) Date of Patent: May 31, 2022

(54) SYSTEM AND METHOD FOR DECODING AND BEHAVIORALLY VALIDATING MEMORY CONSOLIDATION DURING SLEEP FROM EEG AFTER WAKING EXPERIENCE

(71) Applicant: HRL Laboratories, LLC, Malibu, CA (US)

(72) Inventors: Shane M. Roach, San Francisco, CA (US); Praveen K. Pilly, West Hills, CA (US)

(73) Assignee: HRL Laboratories, LLC, Malibu, CA (US)

(*) Notice: Subject to any disclaimer, the term of this patent is extended or adjusted under 35 U.S.C. 154(b) by 763 days.

(21) Appl. No.: 16/199,108

(22) Filed: Nov. 23, 2018

Related U.S. Application Data (63) Continuation-in-part of application No. 15/983,336, filed on May 18, 2018, now Pat. No. 10,835,176, and
(Continued)

(51) Int. Cl.
*A61N 1/36* (2006.01)
*A61B 5/00* (2006.01)
(Continued)

(52) U.S. Cl.
CPC .......... *A61N 1/36025* (2013.01); *A61B 5/316* (2021.01); *A61B 5/369* (2021.01);
(Continued)

(58) Field of Classification Search
CPC .. A61N 1/36025; A61N 1/36031; A61N 1/20; A61N 1/0456; A61N 1/0476;
(Continued)

(56) References Cited

U.S. PATENT DOCUMENTS 5,230,344 A 7/1993 Ozdamar et al.
5,722,418 A 3/1998 Bro
(Continued)

FOREIGN PATENT DOCUMENTS

GB 2 541 947 A 3/2017
KR 10-1114299 B1 3/2012
(Continued)

OTHER PUBLICATIONS

Notification of Transmittal of International Search Report and the Written Opinion of the International Searching Authority for PCT/US2018/014294; dated May 3, 2018.
(Continued)

*Primary Examiner* — Rex R Holmes
(74) *Attorney, Agent, or Firm* — Tope-McKay & Assoc (57) ABSTRACT

Described is a system for decoding and validating memory consolidation. During operation, the system receives electroencephalographic (EEG) data while a subject is performing a specific task. Nuisance signals are then removed from the EEG data, resulting in a nuisance free signal. Skill feature vectors are generated from the nuisance free signal using time-invariant feature extraction. A skill classifier can then be trained for the specific task based on the skill feature vectors to generate a subject specific model regarding a memory replay for the specific task. Finally, electrodes in a neural cap are activated based on the memory replay.

12 Claims, 7 Drawing Sheets

Related U.S. Application Data a continuation-in-part of application No. 15/891,218, filed on Feb. 7, 2018, now Pat. No. 10,716,514, and a continuation-in-part of application No. 15/875,591, filed on Jan. 19, 2018, now Pat. No. 10,736,561, and a continuation-in-part of application No. 15/874,866, filed on Jan. 18, 2018, now Pat. No. 10,744,321, and a continuation-in-part of application No. 15/798,325, filed on Oct. 30, 2017, now Pat. No. 10,796,596, and a continuation-in-part of application No. 15/682,065, filed on Aug. 21, 2017, now Pat. No. 10,720,076, and a continuation-in-part of application No. 15/332,787, filed on Oct. 24, 2016, now Pat. No. 10,307,592.

(60) Provisional application No. 62/483,929, filed on Apr. 10, 2017, provisional application No. 62/620,807, filed on Jan. 23, 2018.

(51) Int. Cl.
*A61N 1/04* (2006.01)
*A61N 1/02* (2006.01)
*A61B 5/316* (2021.01)
*A61B 5/369* (2021.01)

(52) U.S. Cl.
CPC .......... *A61B 5/4836* (2013.01); *A61B 5/7203* (2013.01); *A61B 5/726* (2013.01); *A61B 5/7267* (2013.01); *A61N 1/025* (2013.01); *A61N 1/0408* (2013.01); *A61N 1/0476* (2013.01); *A61N 1/0484* (2013.01)

(58) Field of Classification Search
CPC .............. A61M 21/00; A61M 2230/10; A61M 2205/52; A61M 2021/0055; A61B 5/6814; A61B 5/0476; A61B 5/4836; A61B 5/4812; A61B 5/048; A61B 5/0478; G06T 11/60; G06T 2210/41
See application file for complete search history.

(56) References Cited

U.S. PATENT DOCUMENTS

| | | | |
|---|---|---|---|
| 6,012,926 | A | 1/2000 | Hodges et al. |
| 7,286,871 | B2 | 10/2007 | Cohen |
| 8,478,389 | B1 | 7/2013 | Brockway et al. |
| 8,805,482 | B2 | 8/2014 | Sitzman |
| 8,838,247 | B2 | 9/2014 | Hagedorn et al. |
| 8,938,301 | B2 | 1/2015 | Hagedorn |
| 9,043,993 | B1 | 6/2015 | James |
| 9,089,703 | B2 | 7/2015 | Rodriguez et al. |
| 2004/0131998 | A1 | 7/2004 | Marom et al. |
| 2004/0161121 | A1 | 8/2004 | Chol |
| 2009/0105521 | A1 | 4/2009 | Bentwich |
| 2009/0105785 | A1 | 4/2009 | Wei |
| 2011/0015469 | A1 | 1/2011 | Walter |
| 2011/0093033 | A1 | 4/2011 | Nekhendzy |
| 2012/0036099 | A1 | 2/2012 | Venkatraman et al. |
| 2012/0184868 | A1 | 7/2012 | Shaw |
| 2012/0251989 | A1 | 10/2012 | Wetmore et al. |
| 2012/0265261 | A1 | 10/2012 | Bikson et al. |
| 2012/0277548 | A1 | 11/2012 | Burton |
| 2013/0096363 | A1 | 4/2013 | Schneider et al. |
| 2014/0051045 | A1 | 2/2014 | Stults et al. |
| 2014/0057232 | A1 | 2/2014 | Wetmore |
| 2015/0112409 | A1 | 4/2015 | Hagedorn |
| 2015/0174418 | A1 | 6/2015 | Tyler |
| 2015/0254992 | A1 | 9/2015 | Sethi |
| 2015/0327813 | A1 | 11/2015 | Fu |
| 2016/0256105 | A1 | 9/2016 | Boyle |
| 2016/0361541 | A1 | 12/2016 | Wingeier et al. |
| 2019/0329063 | A1 | 10/2019 | Hendler |

FOREIGN PATENT DOCUMENTS

| | | |
|---|---|---|
| KR | 10-2016-0081454 | 7/2016 |
| WO | WO 03-067555 | 8/2003 |
| WO | WO 2015/153675 A1 | 10/2015 |
| WO | WO 2015/191628 A1 | 12/2015 |
| WO | WO 2016/102602 A1 | 6/2016 |
| WO | WO2016102602 A1 | 6/2016 |
| WO | WO 2016102602 A1 | 6/2016 |
| WO | WO 2016/182947 A1 | 11/2016 |

OTHER PUBLICATIONS

International Search Report of the International Searching Authority for PCT/US2018/014294; dated May 3, 2018.

Written Opinion of the International Searching Authority for PCT/US2018/014294; dated May 3, 2018.

Novakovic, V., et al., "Brain stimulation in post traumatic stress disorder," European Journal of Psychotraumatology, 2011, vol. 2, Article No. 5609, pp. 1-12.

Martin, M., F., et al., "Neuromodulation approaches for the treatment of post-traumatic stress disorder: stimulating the brain following exposure-based therapy," Current Behavioral Neuroscience Reports, 2015, vol. 2, Issue 2, pp. 67-71.

Daly, I., M. Billinger, R. Scherer, and G. Muller-Putz. "On the Automated Removal of Artifacts Related to Head Movement From the EEG." IEEE Transactions on Neural Systems and Rehabilitation Engineering 21, No. 3 (May 2013): pp. 427-434.

Daly, Ian & Pichiorri, Floriana & Faller, Josef & Kaiser, Vera & Kreilinger, Alex & Scherer, Reinhold & Müller-Putz, Gernot (2012). What does clean EEG look like?. Conference proceedings : . . . Annual International Conference of the IEEE Engineering in Medicine and Biology Society. IEEE Engineering in Medicine and Biology Society. Conference. 2012. 3963-3966.

M. Chaumon, D. V. M. Bishop, and N. A. Busch, "A practical guide to the selection of independent components of the electroencephalogram for artifact correction," Journal of Neuroscience Methods, vol. 250, pp. 47-63, Jul. 2015.

Foa EB. Social anxiety disorder treatments: psychosocial therapies. J. Clin. Psychiatry. 2006;67 Suppl 12: pp. 27-30.

Bustos SG, Maldonado H, Molina VA. Midazolam disrupts fear memory reconsolidation. Neuroscience. 2006;139 pp. 831-842.

Chan JCK, LaPaglia JA. Impairing existing declarative memory in humans by disrupting reconsolidation. Proc. Natl. Acad. Sci. 2013;110: pp. 9309-9313.

Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.

Marshall, L, Helgadóttir, H, Molle, M, Born, J. Boosting Slow Oscillations During Sleep Potentiates Memory. Nature. 2006; 444, pp. 610-613.

Cox R, Korjoukov I, de Boer M, Talamini LM. Sound Asleep: Processing and Retention of Slow Oscillation Phase-Targeted Stimuli. PLoS ONE. 2014; 9(7), pp. 1-12.

Weathers, FW, Blake, DD, Schnurr, PP, Kaloupek, DG, Marx, BP, & Keane, TM. The Clinician-Administered PTSD Scale for DSM-5 (CAPS-5). 2013, pp. 1-4.

Rudoy J.D., Voss J.L., Westerberg C.E., Paller K.A. Strengthening Individual Memories by Reactivating Them During Sleep Science. 2009; 326: pp. 1079-1079.

Diekelmann S, Biggel S, Rasch B, Born J. Offline consolidation of memory varies with time in slow wave sleep and can be accelerated by cuing memory reactivations Neurobiol. Learn. Mem. 2012; 98: pp. 103-111.

Jaar O, Pilon M, Carrier J, Montplaisir J, Zadra A. Analysis of Slow-Wave Activity and Slow-Wave Oscillations Prior to Somnambulism. Sleep. 2010; 33: pp. 1511-1516.

Anderson, J. R., Bothell, D., Byrne, M. D., Douglass, S., Lebiere, C., & Qin. Y. An integrated theory of the mind, (ACT-R), Psychological Review 111, (4), 2004, pp. 1036-1060.

Office Action 1 for U.S. Appl. No. 15/798,325, dated Mar. 13, 2019.

(56) References Cited

OTHER PUBLICATIONS

Reiner, Miriam, et al., "Better than sleep: Theta neurofeedback training accelerates memory consolidation," Biological Psychology 95 (2014), pp. 45-53.
Dandamudi, S.P., "Introduction to Assembly Language Programming for Pentium and RSIC Processors," 2005, XXIV, 692p., Hardcover, Ch. 2, pp. 19-44, (2005).
Notification of Transmittal of International Search Report and the Written Opinion of the International Searching Authority for PCT/US2017/059125; dated Feb. 9, 2018.
International Search Report of the International Searching Authority for PCT/US2017/059125; dated Feb. 9, 2018.
Written Opinion of the International Searching Authority for PCT/US2017/059125; dated Feb. 9, 2018.
Notification of Transmittal of International Search Report and the Written Opinion of the International Searching Authority for PCT/US2018/014533; dated May 10, 2018.
International Search Report of the International Searching Authority for PCT/US2018/014533; dated May 10, 2018.
Written Opinion of the International Searching Authority for PCT/US2018/014533; dated May 10, 2018.
L. Deuker, et al., "Memory Consolidation by Replay of Stimulus-Specific Neural Activity," The Journal of Neuroscience, vol. 33, No. 49, pp. 19373-19383, Dec. 4, 2013.
Ji D, Wilson MA. Coordinated memory replay in the visual cortex and hippocampus during sleep. Nat Neurosci. 2007;10: pp. 100-107. doi:10.1038/nn1825.
Schönauer M, Alizadeh S, Jamalabadi H, Abraham A, Pawlizki A, Gais S. Decoding material-specific memory reprocessing during sleep in humans Nat Commun 2017;8: ncomms15404. doi:10.1038/ncomms15404, pp. 1-9.
Belal S, Cousins J, El-Deredy W, Parkes L, Schneider J, Tsujimura H, et al. Identification of Memory Reactivation Turing Sleep by EEG Classification. bioRxiv. 2017; 200436. doi:10.1101/200436, pp. 1-40.
Van Dongen EV, Takashima A, Barth M, Zapp J, Schad LR, Paller KA, et al. Memory stabilization with targeted reactivation during human slow-wave sleep. Proc Natl Acad Sci U S A. 2012; 109: pp. 10575-10580. doi: 10.1073/pnas. 1201072109.
Hashemirad F, Zoghi M, Fitzgerald PB, Jaberzadeh S. The effect of anodal transcranial direct current stimulation on motor sequence learning in healthy individuals: A systematic review and meta-analysis. Brain Cogn. 2016; 102: pp. 1-12. doi:10.1016/j.bandc.2015.11.005.
Marshall L, Helgadóttir H, Mölle M, Born J. Boosting slow oscillations during sleep potentiates memory. Nature. 2006;444: pp. 610 613. doi:10 1038/nature05278.
Chaumon, M., Bishop, D.V.M., and Busch, N.A. (2015). A practical guide to the selection of independent components of the electroencephalogram for artifact correction. J. Neurosci. Methods 250, pp. 47-63.
DARPA RAM—Replay program, found at https: //www. darpa.mil/program/restoring-active-memory, taken on Sep. 10, 2018, pp. 1-2.
Marshall L, Helgadóttir H, Mölle M, Born J. Boosting slow oscillations during sleep potentiates memory. Nature. 2006 444(7119): pp. 610-613.
Rudoy JD, Voss JL, Westerberg CE, Paller KA. Strengthening Individual Memories by Reactivating Them During Sleep Science. Nov. 20, 2009;326(5956): pp. 1079-1079.
Diekelmann S, Biggel S, Rasch B, Born J. Offline consolidation of memory varies with time in slow wave sleep and can be accelerated by cuing memory reactivations Neurobiol Learn Mem. Sep. 2012; 98(2): pp. 103-111.
Rasch BH, Born J, Gais S. Combined blockade of cholinergic receptors shifts the brain from stimulus encoding to memory consolidation. J Cogn Neurosci. May 2006; 18(5): pp. 793-802.
Gais S, Born J. Low acetylcholine during slow-wave sleep is critical for declarative memory consolidation. Proc Natl Acad Sci USA. Feb. 17, 2004; 101(7): pp. 2140-2144.
Rasch B, Buchel C, Gais S, Born J. Odor cues during slow-wave sleep prompt declarative memory consolidation. Science. 2007; 315(5817): pp. 1426-1429.
Kirov R, Weiss C, Siebner HR, Born J, Marshall L. Slow oscillation electrical brain stimulation during waking promotes EEG theta activity and memory encoding Proc. Natl. Acad. Sci. 2009;106: pp. 15460-15465.
Jutras MJ, Fries P, Buffalo EA. Oscillatory activity in the monkey hippocampus during visual exploration and memory formation Proc Natl Acad Sci. Aug. 6, 2013; 110(32): pp. 13144-13149.
Brincat SL, Miller EK. Frequency-specific hippocampal-prefrontal interactions during associative learning. Nat Neurosci. Apr. 2015; 18(4): pp. 576-581.
McNamara CG, Tejero-Cantero A, Trouche S, Campo-Urriza N, Dupret D. Dopaminergic neurons promote hippocampal reactivation and spatial memory persistence Nat Neurosci 2014 12//print; 17(12): pp. 1658-1660.
Ji D, Wilson MA. Coordinated memory replay in the visual cortex and hippocampus during sleep. Nat Neurosci. 2007; 10(1): pp. 100-107.
Kali S, Dayan P. Off-line replay maintains declarative memories in a model of hippocampal-neocortical interactions. Nat Neurosci. 2004; 7(3): pp. 286-294.
Rolls ET. Hippocampo-cortical and cortico-cortical backprojections. Hippocampus. 2000; 10: pp. 380-388.
Creutzfeldt OD, Fromm GH, Kapp H. Influence of transcortical d-c currents on cortical neuronal activity. Exp Neurol. Jun. 1962; 5: pp. 436-452.
Sederberg PB, Kahana MJ, Howard MW, Donner EJ, Madsen JR. Theta and gamma oscillations during encoding predict subsequent recall J Neurosci Off J Soc Neurosci Nov. 26, 2003; 23(34): pp. 10809-10814.
Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.
Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Molle, M. (2013). Auditory closed-loop stimulation of the sleep slow oscillation enhances memory Neuron, 78(3), pp. 545-553.
Office Action 1 for U.S. Appl. No. 15/332,787, dated Sep. 18, 2018.
Response to Office Action 1 for U.S. Appl. No. 15/332,787, dated Nov. 6, 2018.
Notice of Allowance for U.S. Appl. No. 15/332,787, dated Jan. 17, 2019.
Diekelmann S, Biggel S, Rasch B, Born J. Offline consolidation of memory varies with time in slow wave sleep and can be accelerated by cuing memory reactivations. Neurobiol. Learn. Mem. 2012; 98: pp. 103-111.
Kato Y, Endo H, Kizuka T. Mental fatigue and impaired response processes: event-related brain potentials in a Go/NoGo task. Int. J Psychophysiol. Off. J. Int Organ Psychophysiol. 2009; 72: pp. 204-211.
Henckens Mjag, Hermans EJ, Pu Z, Joëls M, Fernández G. Stressed Memories: How Acute Stress Affects Memory Formation in Humans J. Neurosci 2009; 29: pp. 10111-10119.
Akin M, Kurt MB, Sezgin N, Bayram M. Estimating vigilance level by using EEG and EMG signals. Neural Comput. Appl. 2007; 17: pp. 227-236.
Itti L, Koch C. A saliency-based search mechanism for overt and covert shifts of visual attention. Vision Res. 2000; 40: pp. 1489-1506.
Botteldooren D, DeCoensei B. The role of saliency, attentio n and source identification in soundscape research. ProcInternoise 2009 [Internet]. Ottawa, Canada; 2009, pp. 1-9, Available from http://citeseerx.ist.psu.edu/viewdoc/download?doi=10.1.1.468.8119&rep=rep1&type=pdf.
Lebiere C, Pirolli P, Thomson R, Paik J, Rutledge-Taylor M, Staszewski J, et al. A Functional Model of Sensemaking in a Neurocognitive Architecture. Comput. Intell. Neurosci. [Internet], (56) References Cited

OTHER PUBLICATIONS vol. 2013, pp. 1-29, Article ID 921695. Available from: http://www.hindawi.com/journals/cin/2013/921695/abs/.

Euston DR, Gruber AJ, McNaughton BL. The role of medial prefrontal cortex in memory and decision making. Neuron. 2012; 76: pp. 1057-1070.

Jacek P.Dmochowski, LaurentKoessler, Anthony M.Norcia, MaromBikson, Lucas C.Parra (2017). Optimal use of EEG recordings to target active brain areas with transcranial electrical stimulation. NeuroImage, vol. 157, pp. 69-80.

Y Ezzyat, JE Kragel, JF Burke, DF Levy, A Lyalenko, P Wanda, et al. (2017). Direct brain stimulation modulates encoding states and memory performance in humans. Current Biology 27 (9), pp. 1251-1258.

Matthew R. Krause, Theodoros P. Zanos, Bennett A. Csorba, Praveen K. Pilly, Jaehoon Choe, Matthew E. Phillips, Abhishek Datta, and Christopher C. Pack. Transcranial direct current stimulation facilitates associative learning and alters functional connectivity in the primate brain. Current Biology 27, pp. 1-11, Oct. 23, 2017.

Elsa Van Der Loo, Marco Congedo, Mark Plazier, Paul Van de Heyning, Dirk De Ridder. (2007). Correlation between Independent Components of scalp EEG and intra-cranial EEG (iEEG) time series. International Journal of Bioelectromagnetism, vol. 9, No. 4, pp. 270-275.

R. Hyder, N. Kamel, T. B. Tang and J. bornot, "Brain source localization techniques: Evaluation study using simulated EEG data," 2014 IEEE Conference on Biomedical Engineering and Sciences (IECBES), Kuala Lumpur, 2014, pp. 942-947.

Jasmine Song, Colin Davey, Catherine Poulsen, Phan Luu, Sergei Turovets, Erik Anderson, Kai Li, Don Tucker, EEG source localization: Sensor density and head surface coverage, Journal of Neuroscience Methods, vol. 256, 2015, pp. 9-21, ISSN 0165-0270.

A.M. Dale, M.I. Sereno. Improved localization of cortical activity by combining EEG and MEG with MRI cortical surface reconstruction: a linear approach, J Cognit Neurosci, 5 (1993), pp. 62-176.

R. Pascual-Marqui. Standardized low resolution brain electromagnetic tomography (sLORETA): technical details. Methods Find Clin Pharmacol, 24D (2002), pp. 5-12.

Munsif Ali Jatoi, Nidal Kamel, Aamir Saeed Malik, Ibrahima Faye, Tahamina Begum, A survey of methods used for source localization using EEG signals, Biomedical Signal Processing and Control, vol. 11, 2014, pp. 42-52, ISSN 1746-8094, https://doi.org/10.1016/j.bspc.2014.01.009.

Notification of Transmittal of International Search Report and the Written Opinion of the International Searching Authority for PCT/US2017/047865; dated Nov. 27, 2017.

International Search Report of the International Searching Authority for PCT/US2017/047865; dated Nov. 27, 2017.

Written Opinion of the International Searching Authority for PCT/US2017/047865; dated Nov. 27, 2017.

Alex Lilijecrantz, "Memory Consolidation in Artificial Neural Networks," 2 003, https://www.nada.kth.se/utbildning/grukth/exjobb/rapportlistor/2003/rapporter03/liljencrantz_axel_03148.pdf, see pp. 6-7.

International Preliminary Report On Patentability for PCT/US2017/047865; dated Nov. 15, 2018.

Rudoy JD, Voss JL, Westerberg GE, Pallet KA. Strengthening Individual Memories by Reactivating Them During Sleep Science. 2009; 326: pp. 1079-1079.

Anderson, J. R., Bothell, D., Byrne, M. D., Douglass, S., Lebiere, C., & Qin, Y. An integrated theory of the mind. Psychological Review. 2004; 111, 4: pp. 1036-1060.

Hassabis D., Chu C., Rees G., Weiskopf N., Molyneux P.D., Maguire E.A. Decoding Neuronal Ensembles in the Human Hippocampus. Current Biology. 2009; 19(7-3): pp. 546-554.

Notification of International Preliminary Report on Patentability Chapter I for PCT/US2018/014533; dated Oct. 10, 2019.

International Preliminary Report On Patentability Chapter I for PCT/US2018/014533; dated Oct. 10, 2019.

Office Action 1 for U.S. Appl. No. 15/874,866, dated Dec. 10, 2019.
Response to Office Action 1 for U.S. Appl. No. 15/874,866, dated Feb. 19, 2020.
Notice of Allowance for U.S. Appl. No. 15/874,866, dated Apr. 1, 2020.
Office Action 1 for U.S. Appl. No. 15/983,336, dated Mar. 9, 2020.
Response to Office Action 1 for U.S. Appl. No. 15/983,336, dated Jun. 9, 2020.
Notice of Allowance for U.S. Appl. No. 15/983,336, dated Jul. 13, 2020.
Office Action 1 for U.S. Appl. No. 15/891,218, dated Dec. 12, 2019.
Response to Office Action 1 for U.S. Appl. No. 15/891,218, dated Mar. 12, 2020.
Notice of Allowance for U.S. Appl. No. 15/891,218, dated Mar. 27, 2020.
Notification of and the International Preliminary Report on Patentability Chapter 1 for PCT/US2018/014294; dated Oct. 10, 2019.
The extended European Search Report for European Regional Phase Patent Application No. 18775894.1, dated Dec. 3, 2020.
A. Thibaut, et al., "tDCS in patients with disorders of consciousness: Sham-controlled randomized double-blind study," Neurology, Feb. 26, 2014 (Feb. 26, 2014), pp. 1-9.
Response to the extended European Search Report for European Regional Phase Patent Application No. 18775894.1, dated Sep. 30, 2021.
Communication pursuant to Rules 161(2) and 162 EPC for European Regional Phase Patent Application No. 17861769.2, dated May 28, 2019.
Response to the communication pursuant to Rules 161(2) and 162 EPC for European Regional Phase Patent Application No. 17861769.2, dated Dec. 6, 2019.
Correction for Chinese Patent Application No. 201780057906.9, dated Jun. 12, 2019.
The extended European Search Report for European Regional Phase Patent Application No. 18846973.8, dated Mar. 15, 2021.
Marshall L.: "Transcranial Direct Current Stimulation during Sleep Improves Declarative Memory," The Journal of Neuroscience, vol. 24. No. 44, Nov. 3, 2004 (Nov. 3, 2004), pp. 9985-9992.
The extended European Search Report for European Regional Phase Patent Application No. 18775291.0, dated Dec. 8, 2020.
Schouten Daphne I., et al: "State of the art on targeted memory reactivation: Sleep your way to enhanced cognition," Sleep Medicine Reviews. W.B. Saunders, Amsterdam. NL, vol. 32, Apr. 21, 2016 (Apr. 21, 2016), pp. 123-131.
Response to the extended European Search Report for European Regional Phase Patent Application No. 18775291.0 , dated Oct. 23, 2021.
Office Action 1 for U.S. Appl. No. 15/682,065, dated Aug. 14, 2019.
Response to Office Action 1 for U.S. Appl. No. 15/682,065, Dated Dec. 13, 2019.
Notice of Allowance for U.S. Appl. No. 15/682,065, dated Mar. 9, 2020.
Office Action 1 for U.S. Appl. No. 15/875,591, dated Dec. 23, 2019.
Response to Office Action 1 for U.S. Appl. No. 15/875,591, dated Feb. 19, 2020.
Notice of Allowance for U.S. Appl. No. 15/875,591, dated Apr. 10, 2020.
Notification of Transmittal of International Search Report and the Written Opinion of the International Searching Authority for PCT/US2018/033354; dated May 9, 2019.
International Search Report of the International Searching Authority for PCT/US2018/033354; dated May 9, 2019.
Written Opinion of the International Searching Authority for PCT/US2018/033354; dated May 9, 2019.
Notification of and the International Preliminary Report On Patentability Chapter II for PCT/US2018/033354; dated Oct. 22, 2019.
The extended European Search Report for European Regional Phase Patent Application No. 17887539.9, dated Jul. 17, 2020.
Response to the extended European Search Report for European Regional Phase Patent Application No. 17887539.9 , dated Apr. 27, 2021.
Response to Office Action 1 for U.S. Appl. No. 15/798,325, dated May 30, 2019.

(56) References Cited

OTHER PUBLICATIONS

Office Action 2 for U.S. Appl. No. 15/798,325, dated Aug. 9, 2019.
Response to Office Action 2 for U.S. Appl. No. 15/798,325, dated Nov. 12, 2019.
Office Action 3 for U.S. Appl. No. 15/798,325, dated Nov. 21, 2019.
Response to Office Action 3 for U.S. Appl. No. 15/798,325, dated Apr. 7, 2020.
Notice of Allowance for for U.S. Appl. No. 15/798,325, dated Jun. 9, 2020.
International Preliminary Report on Patentability for PCT/US2017/059125; dated Apr. 26, 2019.

SYSTEM AND METHOD FOR DECODING AND BEHAVIORALLY VALIDATING MEMORY CONSOLIDATION DURING SLEEP FROM EEG AFTER WAKING EXPERIENCE

CROSS-REFERENCE TO RELATED APPLICATIONS

The present application is a Continuation-in-Part application of U.S. application Ser. No. 15/891,218, filed on Feb. 7, 2018, entitled, "System and Method For Optimized Independent Component Selection For Automated Signal Artifact Removal To Generate a Clean Signal," now issued as U.S. Pat. No. 10,716,514, which is a non-provisional application of U.S. Provisional Application No. 62/483,929, filed on Apr. 10, 2017, the entirety of which are incorporated herein by reference.

The present application is ALSO a Continuation-in-Part application of U.S. application Ser. No. 15/983,336, filed on May 18, 2018, now issued as U.S. Pat. No. 10,835,176, the entirety of which is hereby incorporated by reference.

The present application is ALSO a Continuation-in-Part application of U.S. application Ser. No. 15/798,325, filed on Oct. 30, 2017, now issued as U.S. Pat. No. 10,796,596, the entirety of which is hereby incorporated by reference.

The present application is ALSO a Continuation-in-Part application of U.S. application Ser. No. 15/332,787, filed on Oct. 24, 2016, now issued as U.S. Pat. No. 10,307,592, the entirety of which is hereby incorporated by reference.

The present application is ALSO a Continuation-in-Part application of U.S. application Ser. No. 15/682,065, filed on Aug. 21, 2017, now issued as U.S. Pat. No. 10,720,076, the entirety of which is hereby incorporated by reference.

The present application is ALSO a Continuation-in-Part application of U.S. application Ser. No. 15/875,591, filed on Jan. 19, 2018, now issued as U.S. Pat. No. 10,736,561, the entirety of which is hereby incorporated by reference.

The present application is ALSO a Continuation-in-Part application of U.S. application Ser. No. 15/874,866, filed on Jan. 18, 2018, now issued as U.S. Pat. No. 10,744,321, the entirety of which is hereby incorporated by reference.

This application ALSO claims the benefit of and is a non-provisional patent application of U.S. Provisional Application No. 62/620,807, filed on Jan. 23, 2018, the entirety of which is hereby incorporated by reference.

GOVERNMENT RIGHTS

This invention was made with government support under U.S. Government ARO contract W911NF-16-C-0018. The government has certain rights in the invention.

BACKGROUND OF INVENTION

(1) Field of Invention

The present invention relates to a memory consolidation system and, more specifically, to a system for decoding and behaviorally validating memory consolidation during sleep from electroencephalographic (EEG) signal data obtained during waking experience in order to control memory intervention.

(2) Description of Related Art

There are no known commercial devices or research that can detect individual replays of a specific memory using non-invasive techniques. Specific memory reactivation in sleep has only been observed from individual neuron recordings in rats (see, for example, Literature Reference No. 1 in the List of Incorporated Literature References). Human sleep studies have been able to differentiate between generalized representations of tasks during periods of sleep from electroencephalographic (EEG) data (see Literature Reference No. 2). However, the human work cannot detect an individual replay period during the night nor what specific skill that individual replay represents.

Another short-coming in previous work has been the inability to validate predictions as ground truth for replay occurrence using non-invasive techniques. Attempts to address this problem in the past have used sensory based targeted memory reactivation (TMR) during sleep as the mechanism for replay initiation and assumed the provided cues guaranteed an associated replay (see Literature Reference Nos. 3 and 4). This is problematic as there is no proof of a one-to-one correspondence between TMR cueing and replay occurrence but rather only an increase in replay probability. Additionally, this treatment only drives the replay of specific skill occurrences but does not provide the ability to detect an individual replay as it is happening endogenously or exogenously. As such these techniques cannot be used to adapt an intervention strategy to target individual skills in real-time.

Additionally, it has been shown that applying transcranial direct current stimulation (tDCS) during sleep in humans can improve performance on memory related tasks (see Literature Reference Nos. 5 and 6). However, these studies and other TMR methods apply the signal in a broadcast fashion with no specificity to the current state of consolidation of the individual. Vital periods of replay are finite and the ability to control and optimize which events are chosen for replay provide for the ability to prioritize specific skill consolidation. Further, targeting specific consolidation events also allows for disruptions of the consolidation process to allow for selective weakening of irrelevant or noxious memories.

Nevertheless, identifying memory replays during sleep is a challenge because: (a) Replays are hidden in a background of other neural activity, muscle activity, and noise; (b) Replay activity may be sparse and may become active at any time during slow-wave sleep (SWS); (c) Replays can occur forwards, backwards, and be temporally compressed; and (d) Replays might change as memory is consolidated.

Thus, a continuing need exists for a system for detecting replays by decoding and behaviorally validating memory consolidation during sleep from EEG signal data in order to control memory intervention.

SUMMARY OF INVENTION

This disclosure is directed to a system for decoding and validating memory consolidation. In various embodiments, the system includes one or more processors and a memory. The memory is, for example, a non-transitory computer-readable medium having executable instructions encoded thereon, such that upon execution of the instructions, the one or more processors perform several operations, such as receiving electroencephalographic (EEG) data (e.g., while a subject is performing a specific task); removing nuisance signals from the EEG data, resulting in a nuisance free signal; generating skill feature vectors from the nuisance free signal using time-invariant feature extraction; and training a skill classifier for the specific task based on the skill feature vectors to generate a subject specific model regarding a memory replay for the specific task, which can be used to inform or otherwise implement an intervention strategy. For example, one or more electrodes in a neural cap are activated based on the memory replay.

In another aspect, the system operates to identifying phases of slow-wave sleep in EEG data to identify phase-locked segments. A feature vector is generated from the phase-locked segments using time-invariant feature extraction. The feature vector is classified for a specific task, the classification including a confidence value. If the confidence value exceeds a predetermined threshold, the phase-locked segments are designated as a memory replay for the specific task.

In yet another aspect, the skill feature vectors include spectral, coherence, and wavelet feature vectors.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a memory consolidation system and, more specifically, to a system for decoding and behaviorally validating memory consolidation during sleep from electroencephalographic (EEG) signal data after waking in order to control memory intervention. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Ji D, Wilson M A. Coordinated memory replay in the visual cortex and hippocampus during sleep. Nat Neurosci. 2007; 10: 100-107. doi:10.1038/nn1825.
2. Schönauer M, Alizadeh S, Jamalabadi H, Abraham A, Pawlizki A, Gais S. Decoding material-specific memory reprocessing during sleep in humans. Nat Commun. 2017; 8: ncomms15404. doi:10.1038/ncomms15404.
3. Belal S, Cousins J, El-Deredy W, Parkes L, Schneider J, Tsujimura H, et al. Identification of Memory Reactivation during Sleep by EEG Classification. bioRxiv. 2017; 200436. doi:10.1101/200436.
4. van Dongen E V, Takashima A, Barth M, Zapp J, Schad L R, Paller K A, et al. Memory stabilization with targeted reactivation during human slow-wave sleep. Proc Natl Acad Sci USA. 2012; 109: 10575-10580. doi:10.1073/pnas.1201072109.
5. Hashemirad F, Zoghi M, Fitzgerald P B, Jaberzadeh S. The effect of anodal transcranial direct current stimulation on motor sequence learning in healthy individuals: A systematic review and meta-analysis. Brain Cogn. 2016; 102: 1-12. doi:10.1016/j.bandc.2015.11.005.

6. Marshall L, Helgadóttir H, Mölle M, Born J. Boosting slow oscillations during sleep potentiates memory. Nature. 2006; 444: 610-613. doi:10.1038/nature05278.
7. Chaumon, M., Bishop, D. V. M., and Busch, N. A. (2015). A practical guide to the selection of independent components of the electroencephalogram for artifact correction. J. Neurosci. Methods 250, 47-63.
8. DARPA RAM-Replay program, found at https://www.darpa.mil/program/restoring-active-memory, taken on Sep. 10, 2018

(2) Principal Aspects

Various embodiments of the invention include three "principal" aspects. The first is a system for decoding and behaviorally validating memory consolidation during sleep from EEG after waking experience. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
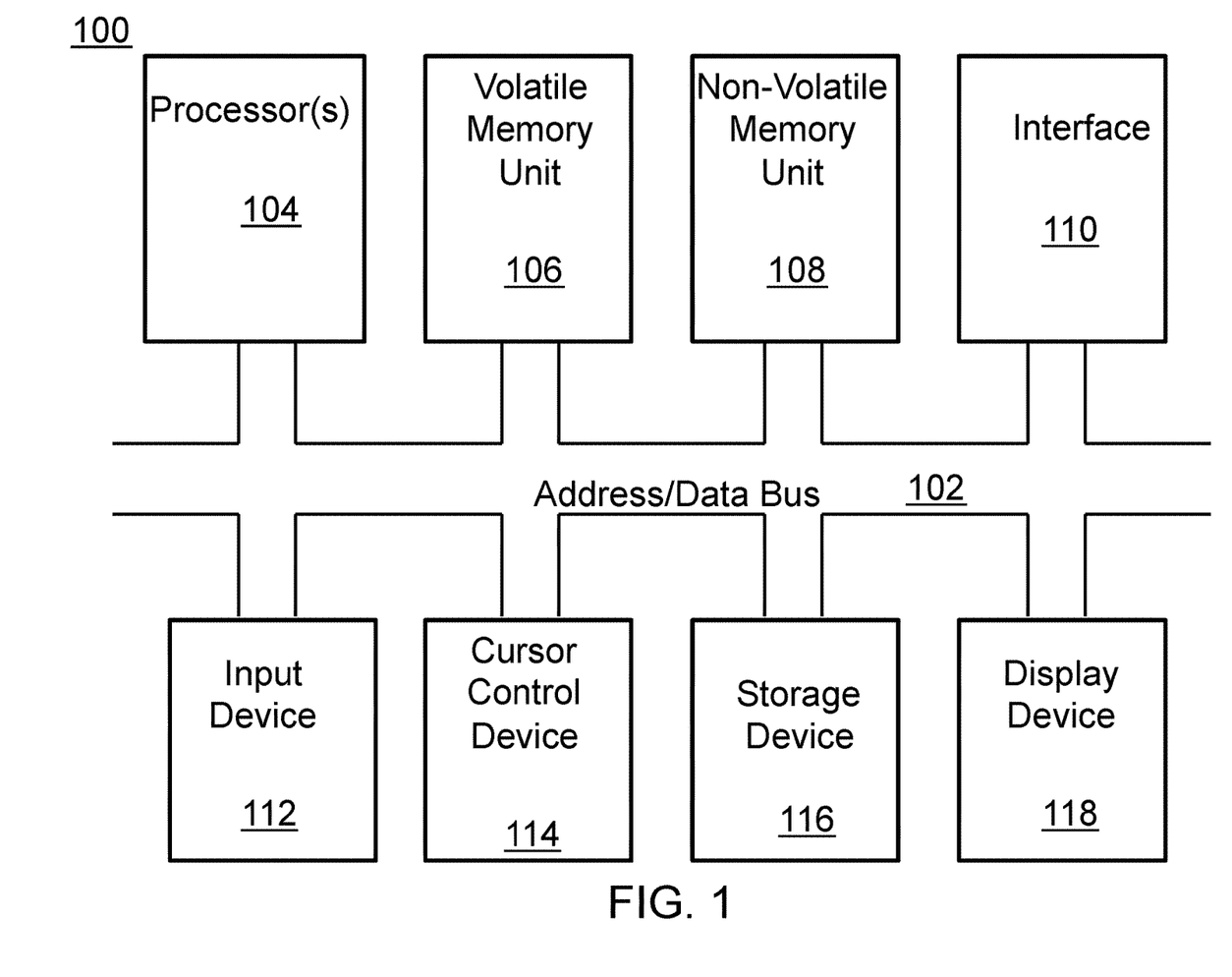
FIG. 1 is a block diagram depicting the components of a system according to various embodiments of the present invention.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
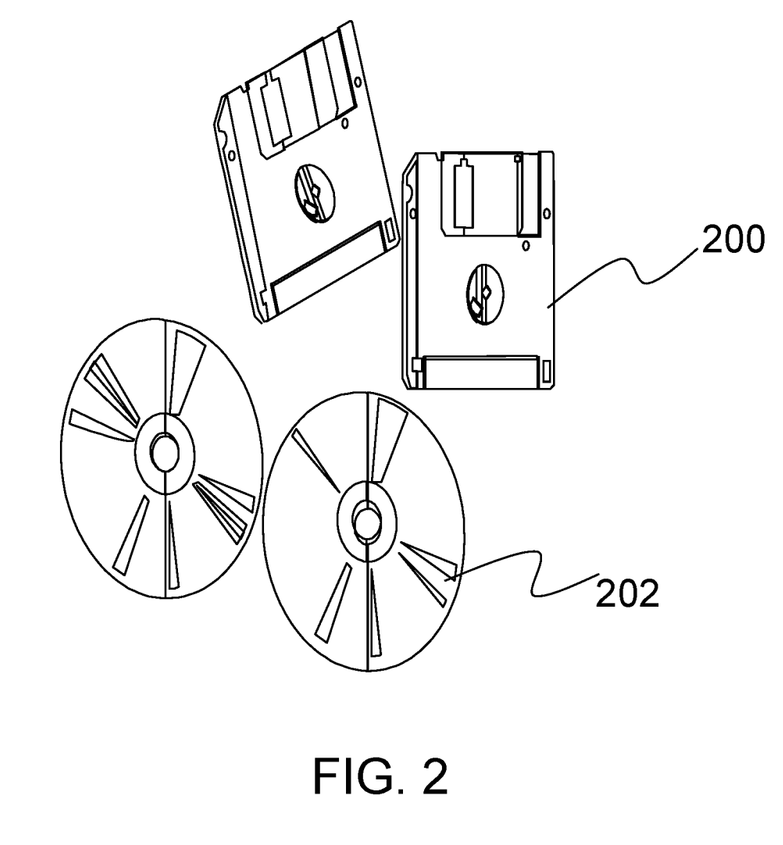
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

This disclosure provides a system that uses electroencephalographic (EEG) signal data recorded during the acquisition of a specific skill or task and EEG data recorded subsequently during sleep to identify the memory replay of the skill of interest during sleep. The instantaneous detection of a specific skill during the night is used to inform an intervention strategy that can dynamically react to the quantity of replays in order to reinforce or disrupt the learning and consolidation of that task. Additionally, summaries of the total detected replay activity for a series of skills are used in following training sessions to customize the training regime and optimize the learning rate for a specific individual to desired skills.

The ability to detect the replay of a specific memory during sleep allows for continuous monitoring of memory consolidation processes and improves the effectiveness of intervention strategies for an individual. Replay events are difficult to detect noninvasively (i.e., from EEG) as the signal characteristics are not well understood and there is no direct way to validate predictions. This disclosure provides a novel discriminative model trained on time invariant features extracted from EEG signals recorded during encoding for evaluating sleep consolidation events. The system can automatically detect neural activity during different phases of slow-wave sleep and per-sequence replay predictions for individual subjects. The system can also correlate predictions with the subject's change in performance on the task to gauge the accuracy of its predictions and constantly refine its models.

The system of the present disclosure can improve mental function and performance on a variety of memory related tasks including but not limited to those involving declarative, procedural, or implicit learning. The ability to identify individual replays during sleep in real-time allows for interventions in the memory consolidation process such as transcranial direct-current stimulation (tCDS) or sensory-based targeted memory recall (TMR) cueing to adapt to and optimize for an individual's learning rate. As a specific memory replay is detected to occur more or less often during the night, the system described herein can trigger an intervention system at the appropriate times to enhance or deteriorate the stabilization of that memory. Additionally, the knowledge of the degree to which memories were consolidated over the night allows for the customization of a training program such that already well fortified skills receive less attention than those that were not learned as well without the need for benchmark testing prior to each lesson.

This system of the present disclosure is suitable for accelerating internal employee training across a wide spectrum of task responsibilities and departments. The system could also be employed to decrease executive or analyst ramp-up time, improve process understanding and compliance for employees, or assist in the training of pilots. Additionally, the system could readily be developed as a commercial learning acceleration device as there exist an array of off-the-shelf component options for EEG collection and intervention strategies using tCDS or audio cueing. Further details regarding the system of this disclosure are provided below.

(4) Specific Details of Various Embodiments

As noted above, this disclosure provides a system that uses electroencephalographic (EEG) signal data to identify the memory replay of a skill of interest. A memory replay is the process of a sequential reactivation of specific activity patterns during rest or sleep that were previously experienced during waking. These replays have been shown to correlate with improved memory formation for the experiences being replayed and are theorized to be a mechanism of consolidation of short-term to long-term memory. The system uses time-invariant features of EEG to make predictions on signals of unknown durations and directionality. These features coupled with discriminative modeling methods capture significant amounts of skill specific representations during waking that are also present during sleep replay. The system also uses an automated methodology to target specific phases of slow-wave sleep in order to limit signal classification to periods of sleep when replays are present. When reduced to practice in experiments, the novel combination specific targeting of slow-wave sleep phases and correlation of model predictions with measured performance change have shown a highly inverse correlation with performance during the second night of sleep for both up and down phases of slow-wave sleep. The average Pearson's linear correlation coefficient (z') of the predicted replay count total through the night paired with the overnight change in performance was −0.55 for the up phase and −0.6 for the down phase.

Figure 3:
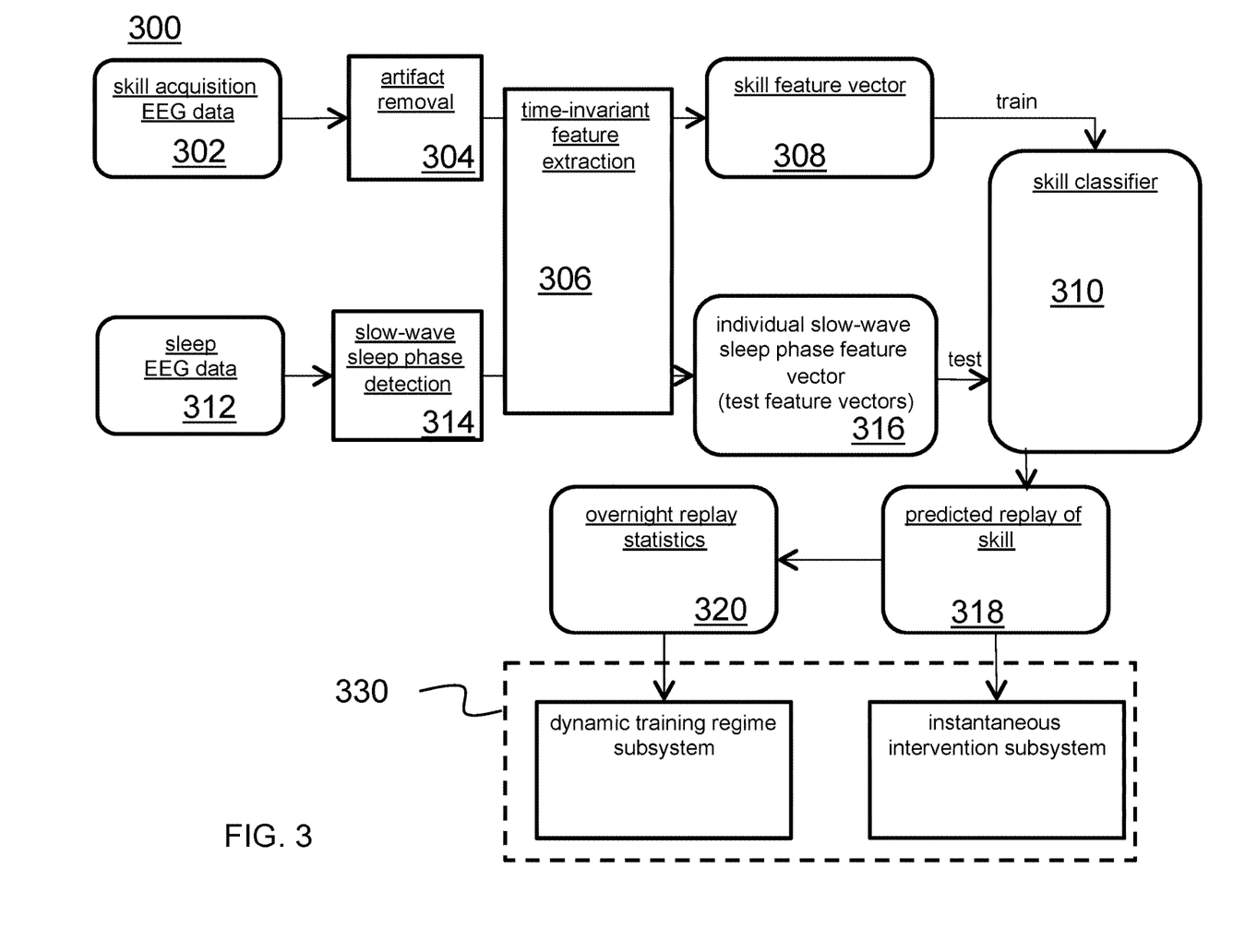
FIG. 3 is a system diagram illustrating a system according to various embodiments of the present invention.

The overall system 300 is shown in the block diagram in FIG. 3. Labeled training data 302 is taken from EEG recorded during a waking task, such as a training session in a flight simulator or a driving task, or any other set task as appropriate given the implementation. A preprocessor performs artifact removal 304 by removing nuisance signals from the EEG. Thereafter, time-invariant feature extraction 306 yields spectral, coherence, and wavelet skill feature vectors 308 that are used as training input to a skill classifier 310. This process results in a model oriented around a specific task and personalized to the individual experiencing the task.

During the night after the individual has trained on their task, a detector 314 identifies phases of slow-wave sleep in sleep EEG data 312 and the phase locked segments become the test data to which the same feature extraction process 306 is applied. A test feature vector 316 of the same time-invariant features calculated in 308 is then classified by the personalized model 310. The resulting confidence from classification is used to identify the predicted replay of skill 318 (i.e., memory replay) for the input phase-locked slow-wave sleep signal. Replay statistics 320 for the sleep session are recorded and used to optimize presentation of material during subsequent learning sessions, such as focusing on aspects of flight for which the subject performed poorly in the flight simulator and fewer replays were detected during the night. The memory replays for the specific task are used in an intervention subsystem 330 to enhance or interfere with specific skill replays during the night, such as through activation of electrodes (on a neural cap) in phase with the identified memory replays (i.e., neural pulses), etc. The system herein can be used with any suitable intervention subsystem 330, non-limiting examples of which are disclosed in U.S. application Ser. No. 15/983,336, filed on May 18, 2018, and entitled, "Personalized Closed-Loop Pulsed Transcranial Stimulation System for Cognitive Enhancement," and U.S. application Ser. No. 15/798,325, filed on Oct. 30, 2017, entitled, "Closed-Loop Intervention Control System," and published as U.S. Patent Publication No. 2018-0068581, the entirety of which are incorporated herein by reference. Each of these aspects are provided in further detail below.

(4.1) Artifact Removal

As noted above regarding the artifact removal process 304, waking EEG data is pre-processed using an optimized independent component selection method for automatic artifact removal and channel selection. Automatic channel rejection is first applied by identifying channels with a normalized joint probability three standard deviations or more above the mean. Remaining channels are re-referenced to the average signal for each channel, DC offset was subtracted, and a 0.1 Hz high-pass filtered is applied. It should be noted that although a specific example is provided, the replay identification and intervention system is not dependent on a specific artifact removal procedure as long as the procedure employed is effective in removing artifacts.

Independent Component Analysis (ICA) decomposition is applied using the logistic infomax algorithm with natural gradient features. Using the SemiAutomatic Selection of Independent Components for Artifact correction (SASICA) plugin for EEGLAB (see Literature Reference No. 7), resulting components that are correlated with known nuisance signals such as eye blinks from electrooculography (EOG), heart beats from electrocardiography (ECG), and head movements from accelerometer sensors are ranked as noise candidates. The remaining components are ranked in random order.

Candidate independent components (ICs) are iteratively subtracted from the source signal and the Signal Quality Index (SQI) is computed before and after IC removal. A Delta SQI is computed by subtracting the SQI of the source signal from the SQI of the signal after IC removal. If the removal of the IC improves the SQI by more than 0.001, that IC is added to a pool of noise-associated ICs. The pool of nuisance ICs are then rejected from the source EEG and the remaining non-artifact components are back-projected into channel space. Finally, rejected channels are interpolated from the remaining channels using spherical interpolation and a moving average subtraction is performed with a window size of 1 second (or any other suitable predetermined window size) to generate a nuisance free signal. This process automatically results in EEG clean of common noise sources such as eye blinks and head movements as well as hard to trace noise sources like sweat artifacts. The artifact removal process is further described in U.S. application Ser. No. 15/891,218, the entirety of which is hereby incorporated herein by reference.

(4.2) Time-Invariant Feature Extraction

As noted above, time-invariant feature extraction 306 is performed on the nuisance free signal (e.g., nuisance free multi-channel EEG data) to yield spectral, coherence, and wavelet skill feature vectors 308 that are used as training input to a classifier 310. Additionally, during the night and after a detector 314 identifies phases of slow-wave sleep in sleep EEG data 312, the phase locked segments become the test data to which the same feature extraction process 306 (described in detail below) is applied to generate a test feature vector 316.

Figure 7:
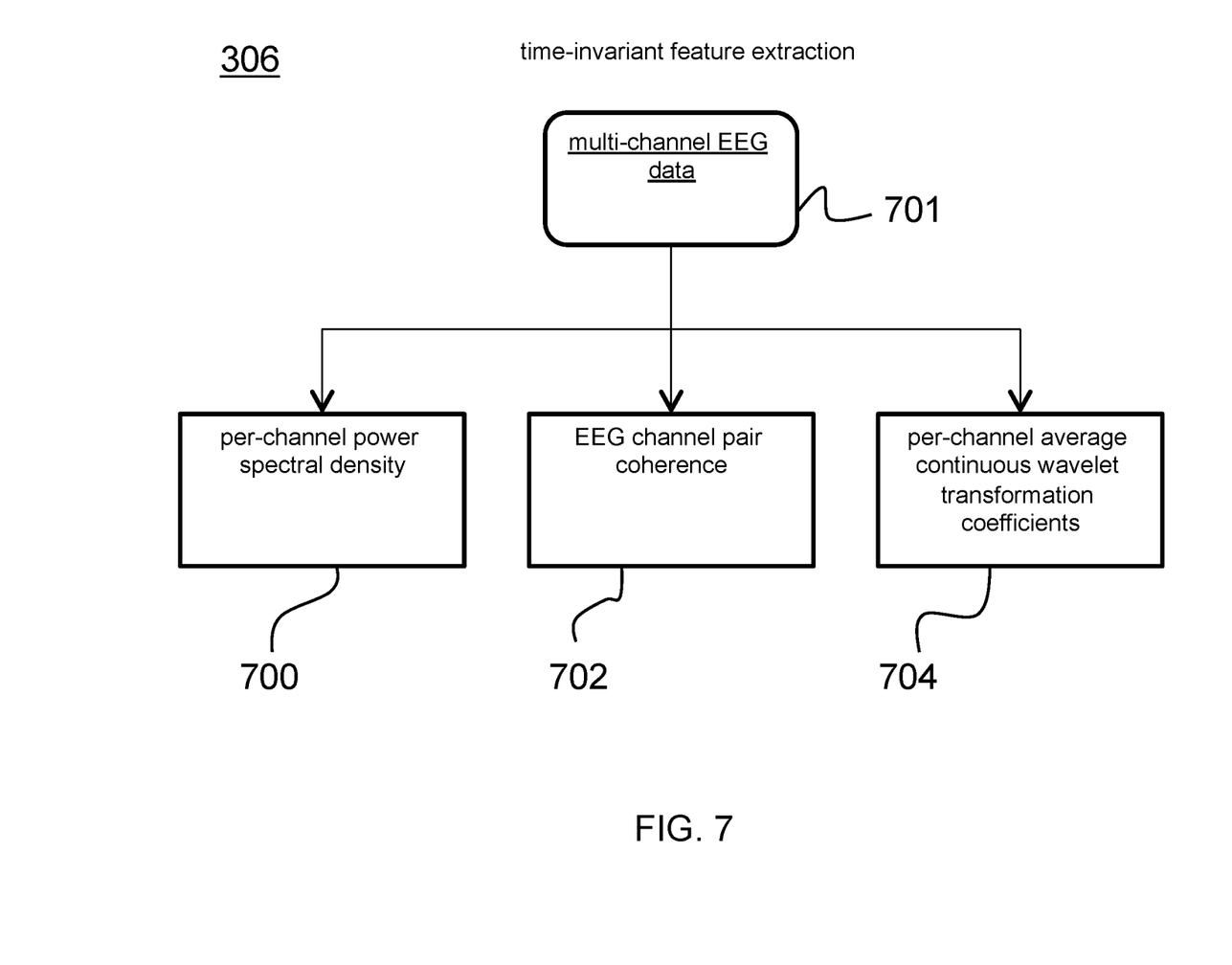
FIG. 7 is a flow chart illustrating time-invariant feature extraction.

The features composing the feature vectors 308 and 316 are power spectral density for each EEG channel, coherence between all EEG channel pairs, and continuous wavelet transformation coefficients for each EEG channel. As shown in FIG. 7, time invariant feature extraction 306 is performed on the multi-channel EEG data 701 to yield the power spectral density 700, channel pair coherence 702, and continuous wavelet transformation coefficients 704 for each EEG channel The average power spectral density for frequencies between 0.5 and 15 Hz is computed for each EEG channel using any suitable technique, such as the FFTW implementation of the Cooley-Tukey algorithm. Every EEG channel-pair combination has mean magnitude of coherence computed for frequencies between 0.5 to 15 Hz using the multi-taper method (or any other suitable coherence method) with a time-bandwidth product of 3 and 5 tapers. It should be noted that although the experimental work described below only considered a particular frequency band, the invention is not intended to be limited thereto as there is no fundamental restriction to such frequencies for the system described herein.

The continuous wavelet transform coefficients are calculated using an analytic Morlet wavelet. For each EEG channel, the average coefficient value for frequencies between 0.5 to 15 Hz is used as the feature input to the skill classifier 310. Separate time-scales are represented in a single model by averaging frequency domain features across a uniform frequency range for each EEG measurement location. The model then defines a skill class as the spatial relation amongst frequency components and can thus identify spatio-temporal patterns in the EEG data between waking and sleep as long as the same EEG measurement locations are maintained between model training and testing.

(4.3) Skill Classifier

The skill classifier 310 operates as a replay assessment model and comprises a discriminative model trained on skill feature vectors 308 that are obtained for each observation of a skill learned during the task of interest. For example, four practice landing sessions in a flight simulator would yield four different training observation feature vectors of the landing skill. Models can be either binary logistic regressors, single, or multi-class classifiers. For binary logistic regressors and single class classifiers, the cascading maximum likelihood structure as detailed below in Algorithm 1 allows for selection of the optimal single skill prediction from multiple one-vs-all predictors. The confidence of the predictions can be adjusted independently and optimized for any one-vs-all discriminative prediction model. Multi-class classifiers can circumvent Algorithm 1 and give only their best fit prediction, or can provide confidence levels for each class to Algorithm 1. In practice, it was noted that ensemble methods such as bootstrap-aggregated decision trees performed best for individuals for which few training samples were obtained during the waking task, but the prediction differences between current state-of-the-art classification techniques were negligible.

Figure 6:
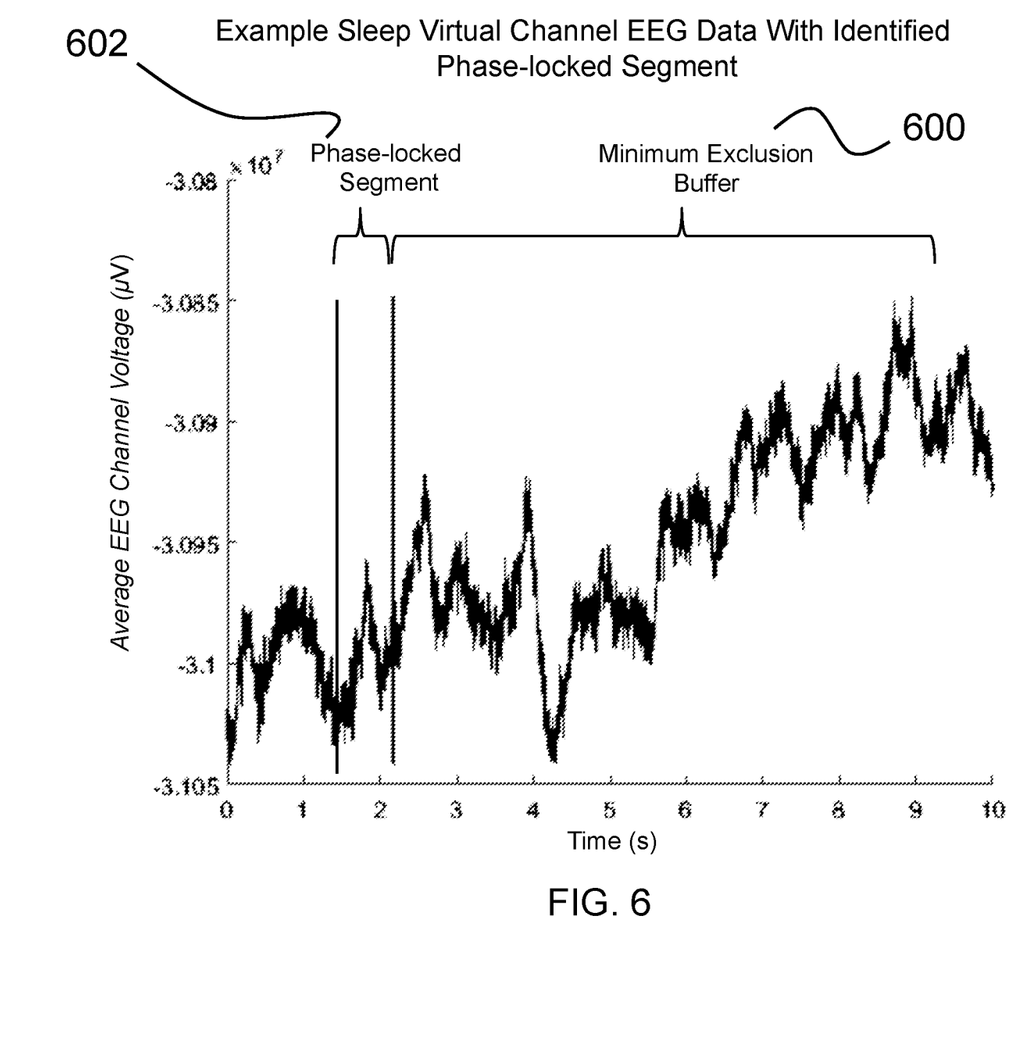
FIG. 6 is a chart illustrating example sleep data with a phase-locked test segment and a subsequent exclusion buffer.

Testing data 312 is taken from EEG recorded during sleep following a training exposure to the task. Sleep data is scored for slow-wave sleep phase using the following automated procedure 314. A virtual-channel comprised of the average signal across all EEG channels is generated which allows for identifying only large, globally active slow-wave oscillation events. Periods during sleep when the ratio of oscillation power in the slow-wave band (0.5-1.2 Hz) to the total power of the virtual-channel signal exceed the median amplitude of slow-wave band activity during stage 3 sleep for a given subject are identified. The dominant frequency during these periods is then used to determine the center frequency from which a Hilbert transform allows for instantaneous phase identification. Finally, the mean squared error between the signal and a generated sine wave with the previously identified parameters is minimized to determine the final slow-wave sleep oscillation (i.e., slow-wave sleep phase detection 314). The phase-locked sleep data is then used as observations from which a feature vector 306 is derived using the same process and parameters as for the skill acquisition data 304. FIG. 6 shows an example virtual channel segment of EEG data captured during sleep. The phase-locked segment 602 was identified using the slow-wave sleep phase detection method 314. A minimum exclusion buffer 600 equal to 5 full cycles of the previously identified phase-locked segment (approximately seven seconds as depicted in FIG. 6), is enforced between detected events of slow-wave oscillations to ensure greater separation between phase-locked test segments 602, as shown in FIG. 6.

The prediction and thresholding of slow-wave sleep feature vectors 316 in the skill classifier 310 are performed according to Algorithm 1 below. The discriminative models trained on waking data are used to predict the confidence of fit of the test observation and the confidence is compared against a threshold. If the background model predicts a confidence above the background threshold then the test observation is labeled background. If it is below threshold the test observation is then compared against each of the skill models in a one-vs-all arrangement. The highest of those prediction confidences is compared against the skill threshold and if it is above the threshold the test observation is labeled with that skill. Confidences below that threshold are labeled background. It is possible to have multiple labels assigned for a given prediction if multiple skill regressors tie for the highest confidence above threshold.

Algorithm 1. Two-Stage, One-Vs-all Replay Classification

Input: test data segment feature vector v, a discriminative model $M_s$ for each skill i in the set of skills S and the background set $M_b$, background confidence threshold $T_b$, and skill confidence threshold $T_s$
$CB=P(M_b|v)$
If $(CB<T_b)$
   For each skill i in S
     $C_i=P(M_i|v)$
   If $(max(C)>T_s)$
     $RP=Skill\ S_i$
Else The system 300 was implemented and tested in a study performed under the DARPA RAM-Replay program (see Literature Reference No. 8). In this study twenty-three subjects were trained on a sequence learning task in a virtual-reality environment and slept in the lab over three nights. EEG data was collected from subjects as they were trained on the task the first evening. The subjects then slept in a monitored lab environment for approximately 8 hours and EEG data was collected for the duration of the sleep session. Subjects were tested on the learned task and performance data in the form of distance to target and reaction time was collected and used to evaluate their learning rate in four sessions after the initial training session: 1) in the morning after the first night, 2) the following evening of the same day as 1, 3) the morning after the second night of monitored sleep, and 4) the afternoon of the same day as 3. The two nights of monitored sleep in the lab were consecutive and thus data from 5 waking sessions (1 training and 4 test) and two sleep sessions of approximately 8 hours each was used to validate the system 300. The models showed cross-validation accuracy of 90.17%±0.49 and the overnight replay prediction totals showed a highly significant, reverse correlation with subject performance on task (z'=0.535 and p=0.001 in a two-tailed t-test that z' distribution is different from zero). These results indicate the system 300 has the ability to accurately predict replays during sleep of specific skills captured during waking task performance. By accurately predicting replays, the system 300 can be implemented with any suitable intervention subsystem to enhance memory consolidation.

(4.4) Control of a Device

Figure 4:
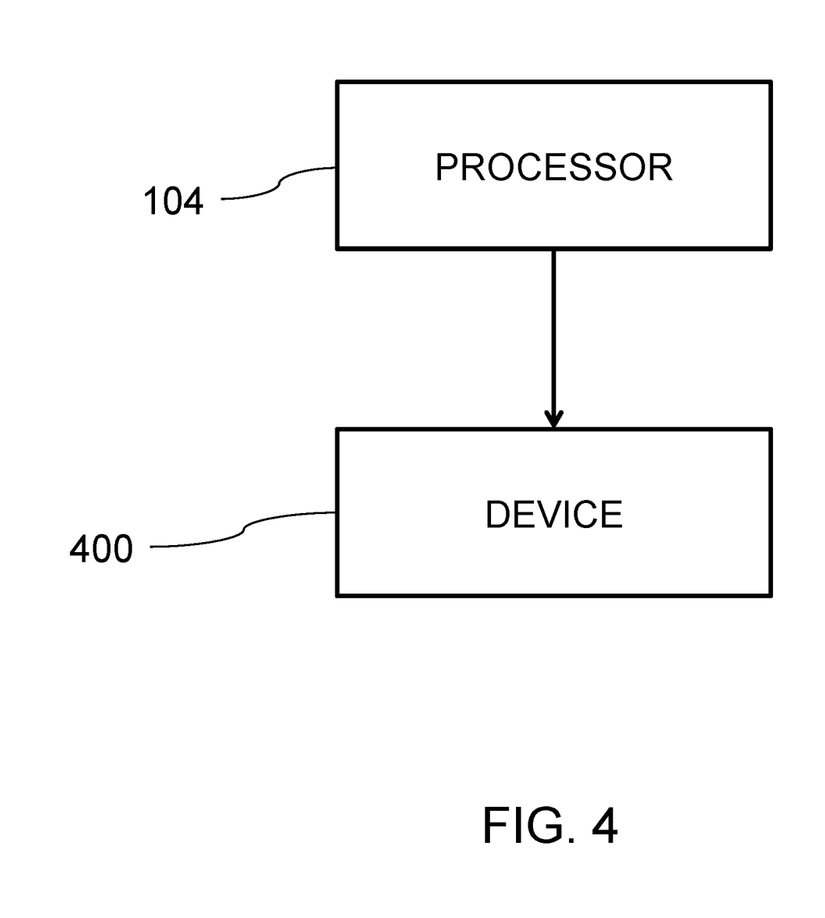
FIG. 4 is a block diagram depicting control of a device according to various embodiments.

As shown in FIG. 4, the system and its processor 104 may be used to control a device 400 (e.g., neural cap having sensors and electrodes, etc.) based on identifying the memory replays to provide neurostimulation according to the intervention subsystems (depicted as element 330 in FIG. 3). As can be appreciated by those skilled in the art, there are a variety of techniques and systems that can be used to provide the neurostimulation and sense the various neural and physiological measures. For example, any suitable neural cap may be used to attach with a subject's head and sense and/or provide the neurostimulation as needed. Non-limiting examples of such an intervention subsystem having sensor and neurostimulation systems (e.g., neural cap) include those as described in U.S. patent application Ser. No. 15/066,813, filed Mar. 10, 2016, and entitled, "System and Method for Training and Assessment," and U.S. patent application Ser. No. 15/148,793, filed May 6, 2016, entitled, "Montage Design for Closed Loop Sensing and Neurostimulation of the Dorsal Lateral Prefrontal Cortex and/or Motor Cortex", both of which are incorporated by reference in their entirety as though fully set forth herein. Other examples of suitable intervention subsystems that can utilize the identify memory replays include the previously noted U.S. application Ser. No. 15/983,336 and U.S. application Ser. No. 15/798,325, filed on Oct. 30, 2017, entitled, "Closed-Loop Intervention Control System," along with the corresponding neural caps, both of which are incorporated by reference in their entirety as though fully set forth herein.

Figure 5:
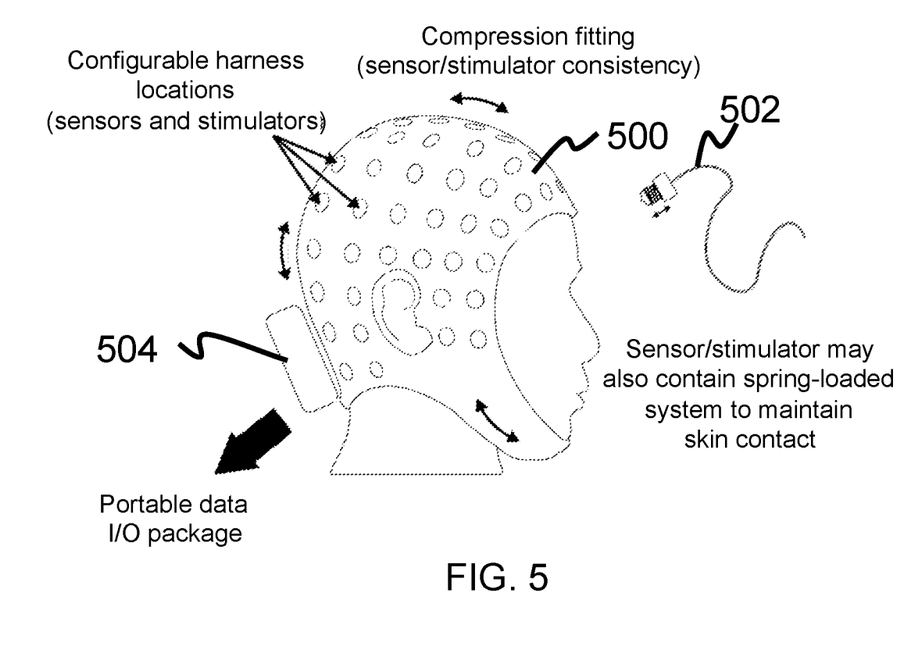
FIG. 5 illustrates a neural cap worn by a human subject for sensing and neurostimulation according to embodiments of the present disclosure.

FIG. 5 illustrates an example device as may be controlled the system described herein. In this example, the device is a neural cap 500 worn by a human subject for sensing and neurostimulation according to embodiments of the present disclosure. As shown, the neural cap 500 may have configurable harness locations for stimulators (electrodes) and sensors. Additionally, the sensor/stimulator may contain a spring-loaded system 502 to maintain skin contact. Compression fitting of the neural cap 500 achieves sensor/stimulator consistency. Furthermore, the neural cap 500 can be connected to portable data input/output (I/O) package 504 that receives data from the system and its corresponding processor 104. Thus, in various embodiments, the system and a corresponding intervention subsystem activate one or more electrodes in the neural cap 500 based on the memory replays. As a non-limiting example, the electrodes are activated to provide an electrical stimulation to the subject in phase with the natural memory replays (neural pulses) when sleeping.

Further non-limiting examples of systems that can implement the processes as described in this disclosure include U.S. Pat. No. 10,046,162, filed on Mar. 16, 2016, and entitled, "Transcranial Intervention to Weaken Traumatic Memories"; U.S. patent application Ser. No. 15/227,922, filed on Aug. 3, 2016, entitled, "Method to Enhance Specific Memories with tCS during Slow-Wave Sleep"; U.S. patent application Ser. No. 15/336,181, filed on Oct. 27, 2016, entitled, "Transcranial Control of Procedural Memory Reconsolidation for Skill Acquisition"; U.S. patent application Ser. No. 15/332,787, filed on Oct. 24, 2016, entitled, "Method and System to Accelerate Consolidation of Specific Memories using Transcranial Stimulation"; U.S. patent application Ser. No. 15/682,065, filed on Aug. 21, 2017, entitled, "Closed-Loop Model-Based Controller for Accelerating Memory and Skill Acquisition"; U.S. patent application Ser. No. 15/875,591, filed on Jan. 19, 2018, entitled, "Neural Model-Based Controller"; and U.S. patent application Ser. No. 15/874,866, filed on Jan. 18, 2018, entitled, "Transcranial Current Stimulation System and Virtual Reality for Treatment of PTSD or Fears," all of which are incorporated by reference as though fully set forth herein.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for decoding and validating memory consolidation, the system comprising:
one or more processors and a memory, the memory being a non-transitory computer-readable medium having executable instructions encoded thereon, such that upon execution of the instructions, the one or more processors perform operations of:
receiving waking task electroencephalographic (EEG) data;
removing nuisance signals from the waking task EEG data, resulting in a nuisance free signal;
generating skill feature vectors from the nuisance free signal using time-invariant feature extraction; and
training a skill classifier for a specific task based on the skill feature vectors to generate a specific model regarding a memory replay for the specific task;
activating one or more electrodes in a neural cap based on the memory replay.

2. The system as set forth in claim 1, further performing operations of: receiving sleep EEG data; identifying phases of slow-wave sleep in the sleep EEG data to identify phase-locked segments; generating a test feature vector from the phase-locked segments using time-invariant feature extraction; classifying the test feature vector for the specific task, the classification including a confidence value; and if the confidence value exceeds a predetermined threshold, then designating the phase-locked segments as a memory replay for the specific task.

3. The system as set forth in claim 2, wherein the skill feature vectors include spectral, coherence, and wavelet feature vectors.

4. The system as set forth in claim 1, wherein the skill feature vectors include spectral, coherence, and wavelet feature vectors.

5. A computer program product for decoding and validating memory consolidation, the computer program product comprising:
a non-transitory computer-readable medium having executable instructions encoded thereon, such that upon execution of the instructions by one or more processors, the one or more processors perform operations of:
receiving waking task electroencephalographic (EEG) data;
removing nuisance signals from the waking task EEG data, resulting in a nuisance free signal;
generating skill feature vectors from the nuisance free signal using time-invariant feature extraction; and
training a skill classifier for a specific task based on the skill feature vectors to generate a specific model regarding a memory replay for the specific task;
activating one or more electrodes in a neural cap based on the memory replay.

6. The computer program product as set forth in claim 5, further comprising instructions for causing the one or more processors to perform operations of: receiving sleep EEG data; identifying phases of slow-wave sleep in the sleep EEG data to identify phase-locked segments; generating a test feature vector from the phase-locked segments using time-invariant feature extraction; classifying the test feature vector for the specific task, the classification including a confidence value; and if the confidence value exceeds a predetermined threshold, then designating the phase-locked segments as a memory replay for the specific task.

7. The computer program product as set forth in claim 6, wherein the skill feature vectors include spectral, coherence, and wavelet feature vectors.

8. The computer program product as set forth in claim 5, wherein the skill feature vectors include spectral, coherence, and wavelet feature vectors.

9. A computer implemented method for decoding and validating memory consolidation, the method comprising an act of:
causing one or more processors to execute instructions encoded on a non-transitory computer-readable medium, such that upon execution, the one or more processors perform operations of:
receiving waking task electroencephalographic (EEG) data;

removing nuisance signals from the waking task EEG data, resulting in a nuisance free signal;

generating skill feature vectors from the nuisance free signal using time-invariant feature extraction; and training a skill classifier for a specific task based on the skill feature vectors to generate a specific model regarding a memory replay for the specific task activating one or more electrodes in a neural cap based on the memory replay.

10. The method as set forth in claim 9, further performing acts of: receiving sleep EEG data; identifying phases of slow-wave sleep in the sleep EEG data to identify phase-locked segments; generating a test feature vector from the phase-locked segments using time-invariant feature extraction; classifying the test feature vector for the specific task, the classification including a confidence value; and if the confidence value exceeds a predetermined threshold, then designating the phase-locked segments as a memory replay for the specific task.

11. The method as set forth in claim 10, wherein the skill feature vectors include spectral, coherence, and wavelet feature vectors.

12. The method as set forth in claim 9, wherein the skill feature vectors include spectral, coherence, and wavelet feature vectors.

* * * * *